United States Patent [19]

Salort

[11] 4,422,453

[45] Dec. 27, 1983

[54] EXTERNAL APPARATUS FOR VERTICAL STANCE AND WALKING FOR THOSE WITH HANDICAPPED MOTOR SYSTEMS OF THE LOWER LIMBS

[76] Inventor: Guy J. Salort, 219, rue Raymond Losserand, 75014 Paris, France

[21] Appl. No.: 382,250

[22] Filed: May 26, 1982

[30] Foreign Application Priority Data

Jun. 15, 1981 [EP] European Pat. Off. ............ 81400949
Jun. 1, 1981 [FR] France ................................ 81 10764

[51] Int. Cl.$^3$ .............................................. A61F 5/04
[52] U.S. Cl. ................................................ 128/80 G
[58] Field of Search ................. 128/80 G, 80 R, 80 F, 128/87 R

[56] References Cited

U.S. PATENT DOCUMENTS 4,169,467 10/1979 Rabischong et al. ............ 128/80 G
4,296,761 10/1981 Tyo .................................. 128/80 G

FOREIGN PATENT DOCUMENTS 85765 3/1921 Austria ............................. 128/80 G

*Primary Examiner*—John D. Yasko
*Attorney, Agent, or Firm*—Brisebois & Kruger

[57] ABSTRACT

Apparatus for use by a person suffering handicap of the motor system of one or two lower limbs includes a one-piece corset connected to at least one knee piece by a respective external resilient metallic femoral lever, the knee piece being, in turn, connected to a respective orthopaedic boot by means of an internal resilient metallic tibial lever. The femoral and tibial levers are capable of absorbing torsional and flexural stresses and the restoring movements they provide serve as motive force for a walking movement.

14 Claims, 6 Drawing Figures

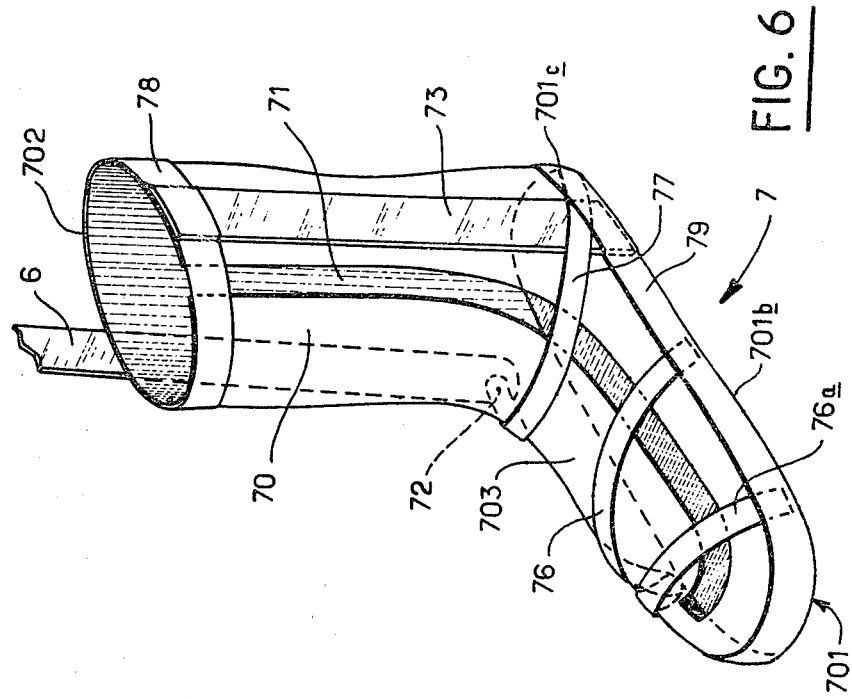
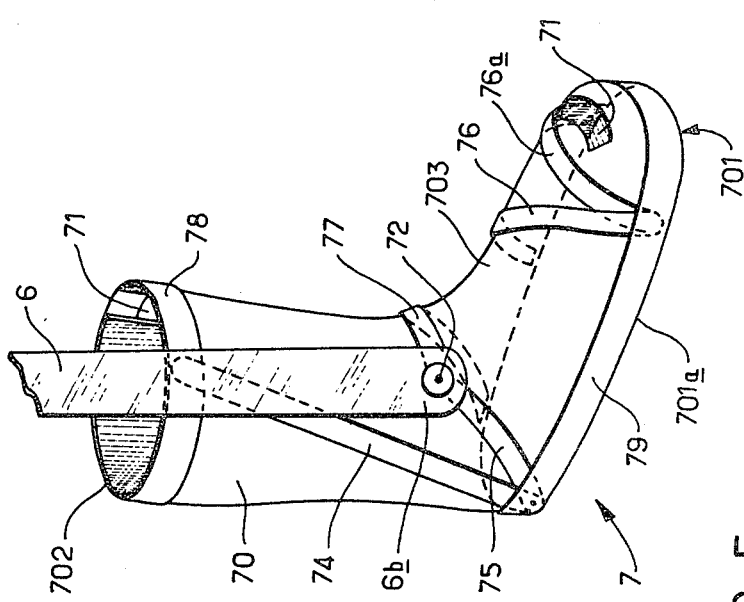

EXTERNAL APPARATUS FOR VERTICAL STANCE AND WALKING FOR THOSE WITH HANDICAPPED MOTOR SYSTEMS OF THE LOWER LIMBS

DESCRIPTION

Field of the Invention

The present invention relates to an external apparatus for a vertical stance and walking for a person with handicap of the motor systems of one or both lower limbs.

More precisely, the object of the present invention is to provide apparatus to allow a vertical stance and locomotion for those with handicapped motor systems of the lower limbs by means of an independent apparatus constituted by a detachable and light supporting structure making it possible at one and the same time to mitigate the inadequacy of postural tonus and to reconstitute the physiological mechanism of the podal support and walking.

SUMMARY OF THE INVENTION

Thus the present invention provides an external apparatus for a vertical stance and walking for a person with handicap of the motor system of one or of two lower limbs, comprising in combination: (a) a single-piece corset disposed at the height of the pelvic girdle of the wearer; (b) parallel to the external side of the femur of the wearer and over its length, an external femoral lever comprising a flexible metal strip capable of absorbing and restoring flexural and torsional stresses; (c) at knee level of the wearer, a knee piece capable of maintaining the relative movement between the thigh and the leg with a slight flexion and a slight valgus state within the strict limits of the physiological articular play; (d) parallel to the antero-internal side of the tibia of the wearer and throughout its length, an antero-inner tibial lever comprising a strip of flexible metal capable of absorbing and restoring the flexural and torsional stresses; (e) a first elastic strap connecting the upper end of the outer femoral lever, substantially as the extension of the outer femoral lever, to the said corset near the iliac crest of the wearer; (f) a second elastic strap extending transversely in a slightly upwardly inclined slope connecting the outer femoral lever to the corset towards or in the direction of the iliac spines of the wearer, the said second elastic strap thus substantially crossing the pubic symphysis of the wearer; (g) means connecting the lower end of the outer femoral lever to the knee piece; (h) means connecting the upper end of the antero-inner tibial lever to the knee piece; and (i) means limiting the articular play of the tibio-tarsal articulation of the wearer, and connected to the lower end of the tibial lever.

In the case where the motor handicap affects only a single lower limb, the apparatus need comprise only a single set of elements applied to this limb, in addition to the corset. If, on the other hand, the handicap affects both the lower limbs, each limb carries the corresponding elements.

The apparatus according to the invention in fact produces a veritable reversal of the physiological system of the lower limb and is thus radically distinguished from the known prostheses which strive to ensure a supporting action taking over the whole limb whereas in the invention, the limb participates in a direct way, so to speak, in the process.

Thanks to the apparatus according to the invention, automatic walking becomes possible by means of the voluntary displacement of the centre of gravity of the body rearwards and sideways, in the way of a "pelvic motor" to reproduce the natural walking action which is only a series of prevented falls. By means of the amplitude modulation of its movements which are preadjusted, the apparatus ensures the recentering of the bodily weight according to the subject's skeletal axis and the absorption of the forward movement by inertia so that the limits of the polygon of equilibrium should not be exceeded and a fall is avoided.

The single piece corset is only slightly deformable, or not deformable at all, to ensure the semi-rigidity of the lower part of the trunk and to make it possible to ensure the forward motion by the displacement of the part of the trunk situated above the corset. The corset also serves to improve the liaison between the part of the apparatus extending parallel to the femur and pelvis, especially at the level of the iliac wings of the wearer.

Advantageously, the external femoral lever extends between the upper sub-trochanteric end and a lower end disposed substantially above the femoral condyle of the wearer.

The tibial lever, in the antero-internal position, advantageously extends between an upper end disposed below the tibial plate and a lower supra-malleolar end.

Preferably, the knee piece forms a single flexible piece formed by three parts: a lower femoral cone, an upper tibial cone and a para-patellar cone between them. One might consider making this knee piece of two or three distinct elements interconnected by appropriate, preferably elastic, means. The means allowing the articulation of the knee in slight flexion and slight valgus positions preferably comprise a system of suitably disposed elastic straps to form elastic restraints to recurvation, to the varus and valgus states, and to flexion. These elastic straps are preferably adjustable so as to adapt the knee piece to each precise case to maintain the articulation in slight flexion and slight valgus positions. The flexion may, for instance, be of the order of 120° to 160° and advantageously be such that in the state of rest, when the subject is upright, the tibial plate forms an angle with the horizontal plane towards the back and towards the front which should not be less than 5°. Similarly, the valgus angle of the plate should preferably be equal to or greater than 5° relative to the horizontal. The knee piece according to the invention is also designed to form a restraint to internal and external rotations and to have the tendency of favouring the internal rotation, thus stabilising the femoral head to ensure a recentering with each step, the lower limb being, in fact, subjected to an internal screwing stress during its movement.

By way of example, for a subject weighing 40 kg, the tension of the elastic straps of the apparatus could be approximately 0.6 Newtons.

In a preferred embodiment, the means for limiting the articular free play of the tibio-tarsal articulation is an orthopaedic boot. Provision may be advantageously made for the orthopaedic boot to comprise: (i) a semi-rigid shell, defining a sole and a vamp, and surrounding the foot and the bottom tibial cone of the wearer; (ii) means defining an opening in said shell, said opening extending opposite the antero-external accommodation of the tibial cone and opposite the outer edge of the foot of the wearer, above the cuboid and at least one metatarsal range; (iii) securing means on said shell, in the zone of the internal malleolus of the wearer, for the bottom end of the tibial lever of the apparatus; (iv) an elastic supporting means comprising, on the one hand, a spring strip connected to the shell and disposed vertically opposite the fibula of the wearer, from the external side of the calcaneus as far as the zone of the upper edge of the shell and, on the other hand, elastic adjusting means outside the shell, extending firstly from the inner edge of the sole of the shell towards the top part of the vamp and towards the top edge of the leg of the shell and secondly, from said fixing means for the tibial lever to the postero-external zone of the heel of the sole; and (v) means for closing the shell of the boot.

Advantageously, the means for closing the shell comprise an elastic means stretched between the internal edge of the sole of the shell, at the level of the first metatarsal, and the external edge of the sole at the level of the cuboid of the wearer; contingently, the closing means for the shell may comprise elastic means stretched between the inner edge of the sole of the shell, at the level of the first metatarsal, and the outer edge of the said sole at the level of the fifth metatarsal. At the foot end, the opening in the shell extends transversely above the last two metatarsals. The shell surrounds the lower tibial cone as far as the top of the lower third of the leg and the closing means comprise a tightening band extending all along the top edge of the leg of the shell. The shell of the boot may be integrally moulded of a plastic material; the boot may internally comprise a supporting sole for the foot, moulded to the shape of the plantar arch of the user, when placed in a vertical equilibrium position.

The orthopaedic boot defined above ensures the physiological functioning of the podal support as strengthener and as regulator of an internal screwing motion which improves the functioning of the apparatus according to the invention. The spring strip, connected to the boot shell and disposed vertically opposite the fibula, may be a tempered steel strip approximately 40 mm wide and 1 mm thick; this spring strip regulates the movements of inner inclination (rotation and lowering of the calcaneus) and the internal screwing movements of the tibial segments on the tibio-tarsal and sub-astragalar articulations. The elastic adjusting means which are connected to the spring strip of the shell, regulate the actions of the spring strip of the shell and of the inner tibial spring lever. It has been found that this particular design of the boot makes it possible to absorb slight deformations in the internal screwing motions and to restore these stresses elastically: there follows therefrom a slight physiological flexion of the ankle as well as the progress of the podal step (heel-external edge-internal edge).

BRIEF DESCRIPTION OF THE DRAWINGS

Other objects and advantages of the present invention will emerge from a reading of the following description, given by way of a non-restrictive example, with reference to the accompanying drawings. In these drawings:

FIG. 5 is a perspective detail of a boot of the apparatus according to the invention, viewed from the inner side; and FIG. 6 shows the boot of FIG. 5, in perspective, viewed from the outer side;

DESCRIPTION OF THE PREFERRED EMBODIMENT

Figures 1, 4:
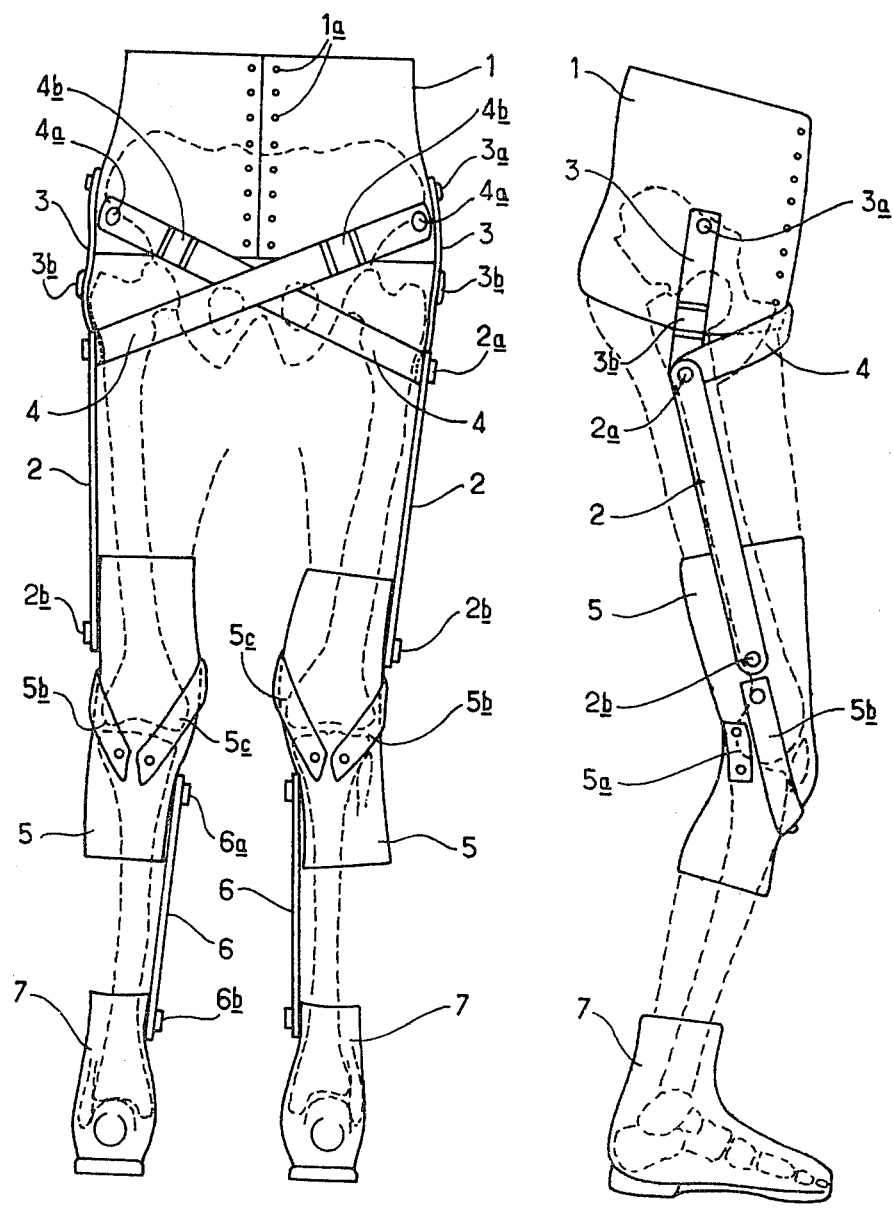
FIG. 1 is a schematic anterior view of an apparatus according to the invention.
FIG. 4 is an external side view of the part of the apparatus of FIG. 1 corresponding to one of the lower limbs.
Figures 2, 3:
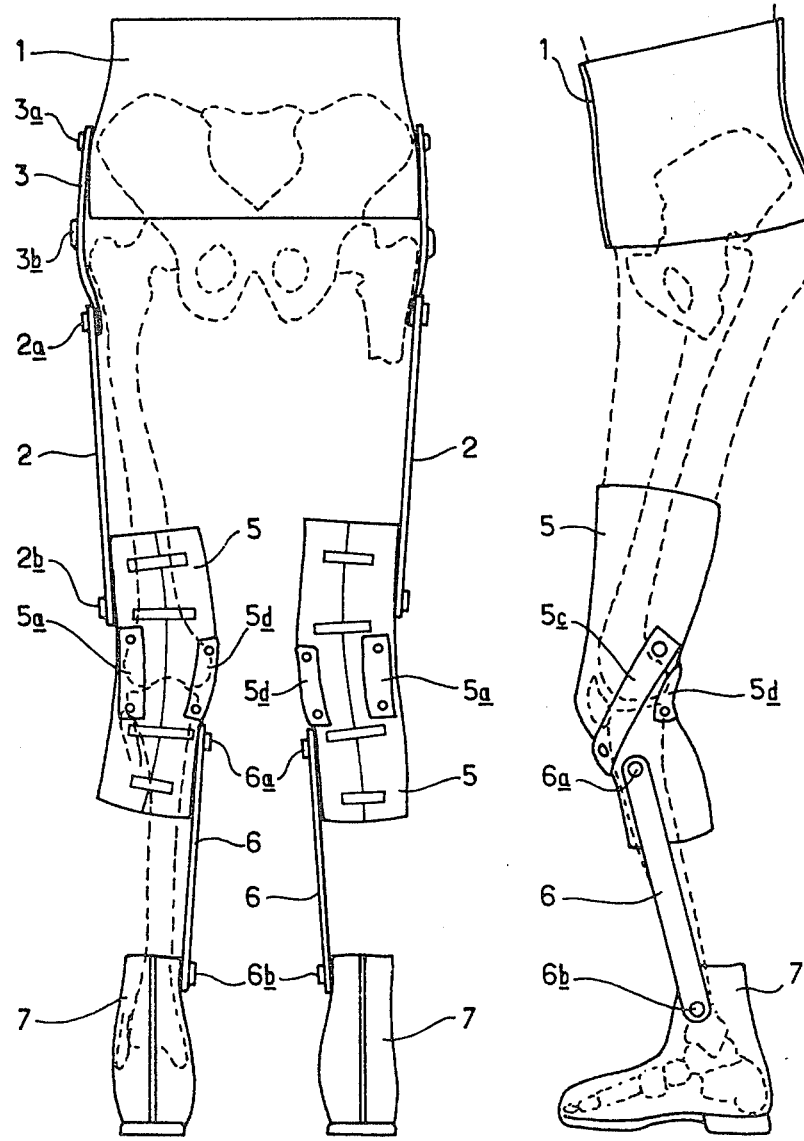
FIG. 2 is a schematic posterior view of the apparatus of FIG. 1.
FIG. 3 is an internal side view of the part of the apparatus of FIG. 1 corresponding to one of the lower limbs.

The apparatus shown comprises a single piece corset 1 surrounding the pelvis and abdomen and of sufficient vertical extent to ensure the liaison between the centre of gravity of the body and the lower limbs. This corset may advantageously open at the front and may, for this purpose, be provided with buttonholes 1a allowing the corset to be closed in the laced-up state. As will be seen in the drawing, the top edge of the corset is situated at a slightly supra-umbilical level whilst the bottom edge of the corset substantially passes at the supra-trochanteric level. Each femoral lever 2 is formed by a relatively rigid rectilinear strip which is sufficiently elastic to be capable of absorbing flexional and torsional stresses and to provide restoring moments in order to fulfil the function of an energy accumulator. The lever 2, is, for instance, formed of a light metal such as the metal known as Dural, and is 3 mm thick and 25 mm wide. Depending on the tonus of the subject it may be preferable to use tempered steel strips. It extends down the outer side of the thigh, substantially parallel to the femur, with its upper end 2a at a slightly sub-trochanteric level and its lower end 2b terminating substantially above the femoral condyle.

The upper end 2a is connected to the lower end of an elastic strap 3 whose top end is fixed at 3a to the corset 1 at the level of the iliac crest, preferably substantially at the level of the anterior tuberosities. This top end 2a is, moreover, connected to an elastic strap 4 which rises slightly and proceeds towards the opposite hip to be fixed to the corset at 4a, for instance at the level of the iliac spine.

Provision is made for means 3b, 4b to allow the length of the straps 3,4, to be adapted and adjusted.

The various elastic straps 3, 4, the corset 1 and the femoral levers 2 thus form a pelvic motor system whose functioning will be described below.

The bottom end 2b of each femoral lever 2 is connected to a respective knee piece 5 whose function is, on the one hand, to ensure transmission of the forces between the femoral levers and the tibial levers and, on the other hand, to control the scope of the articular displacement of the knee articulation within the strict physiological limits of free motion.

For this purpose the knee piece 5, consisting for instance of a relatively flexible material, comprises elastic restraints in the form of elastic straps, preferably adjustable in length, which are intended to allow a slight articular deflection and to ensure comfort in walking. The first strap 5a extends the lower end 2b of the femoral lever 2 downwardly, passing on the femoral tibial articular interlineation and covering the external posterior side of the external condyle and the lateral surface of the tibial plate. This strap 5a constitutes a restraint to recurvation and the varus state.

Strap 5b, which is longer, lies on an extension of a force line extending the bottom end 2b of the outer femoral lever, passing bridge-wise on the external surface of the external condyle, the interlineation, the external tibial plate outside the anterior parapatellar cone, and finally being inserted in a subpatellar position opposite the patellar tendon. This strap 5b constitutes a restraint to flexion and internal rotation, and ensures the outer stability of the parapatellar cone.

The third restraint is constituted by strap 5c which extends from the patellar tendon rising upwards and inwards to bridge the interlineation and the inner side of the inner condyle to terminate substantially above and behind the inner condyle. This is a restraint to flexion, the valgus state and inner rotation. It ensures the stability of the parapatellar cone.

The fourth restraint 5d stretches from the inner side of the tibia at the level of the insertion of the inner tibial lever and extends towards the posterior top of the inner condyle, covering its posterior side. It is a restraint to inner rotation, to recurvation and to the valgus state.

These various restraints are adjusted so as to maintain the tibial plate normally in a flexed position inclined at least 5° in relation to the horizontal and in a state of valgus of preferably 5° in relation to the horizontal. In other words this knee piece position imparts to and regulates an internal screwing motion on the lower carrying limb. The flexion makes it possible to ensure that the body weight always has the tendency to produce a forward sliding towards the valgus state to obtain a recentering of the load via the lower limb by an internal screwing motion.

The adjustments of the various restraints 5a, 5d are obviously effected according to the state of the knee which may itself be permanently deformed, especially in the varus and recurvation states.

The tibial lever 6 is inserted at 6a on the knee piece in an antero-internal position and extends along the tibial diaphysis as far as its bottom end 6b at the level of the internal malleolus, where it is fixed on the rising leg of an orthopaedic boot 7.

It will therefore be understood that when the subject wearing the apparatus is in an upright position, as shown in the drawing, the lower limb is maintained in this position by the orthopaedic boot 7 and the knee piece 5, which limit scope for free tibial-tarsal and femoral-tibial articulations, the maintenance of the position between the thigh and pelvis being ensured by the corset, the straps 3 and 4, and the cerebellar regulation of posture. It will, however, be understood that, in this position, the femoral levers 2 and tibial levers 6 make up for the lack of muscular tonus because relative movements proceeding from the position represented in the drawing will produce a deformation of the springs to exert an opposite stress by way of reaction. According to the postural tonus condition of the subject, an appropriate prestressing may be applied to the levers 2 and 6 (for instance, some deciNewtons).

In this position, the moving unit formed by the trunk, the head, and the upper limbs may find two points of support at the level of the femoral heads in their acetabula. Proceeding from the position of equilibrium shown in the drawing, displacement of the centre of gravity sideways and rearwards is only possible if the support region, which must be femoral, receiving the progressive displacement of the load, is capable of presenting a series of supporting points for this load, based on dynamic resistance in an opposite sense and direction. When one of the legs leaves the ground under the effect of the voluntary disequilibrium created in this way, the absorption of the doubling of the load on the other lower limb is effected by the flexible femoral lever 4 and the corresponding inner flexible tibial lever 5. The flexible levers 4 and 5 which are thus deformed will then be able to provide a progressive stress restoring effect in time and space as the load passes on to the other support, thereby releasing a propulsive force directed towards the front, inside and low down. The effect of the vertical lateral straps 3 is to limit the hip movement and to recentre the load and to allow it to be adjusted on the femoral head by exerting a pull on the lower structures of the para-skeleton of the corresponding limb and also by increasing the internal screwing compression. Thus, on each sideways and backward displacement of the centre of gravity towards a femoral head, the corresponding pelvic acetabulum will describe, together with the load it supports, a circular motion in the sense and direction opposite to that of the support given by the femoral head. This movement will be controlled by the crossed straps 4 and one thus obtains a system consisting of three fixed points actuated by the top voluntary lever, that is to say, the two anterior iliac spines and the pubis so that the thrusts of the pubis are transmitted automatically to the two fixed points of the iliac spines and to the two dynamic supports constituted by the outer femoral levers. This creates a differential system around an axis passing through the coxo-femoral articulations actuated by the top voluntary lever, thus creating a pelvic inertia-based motor system allowing automatic walking.

A particular embodiment of the boot 7 of the apparatus according to the invention has been shown in detail in FIGS. 5 and 6. The boot is constituted by a shell 70 made of a moulded plastic material, of a thickness of 3 mm, for instance of low density polyethylene (d=0.95). This shell, made of a single piece, is formed by a sole 701 surmounted by a vamp, whose upper part has been designated as 703 and by a leg whose upper edge 702 is intended to be located slightly higher than one third of the way up the human leg. The leg and vamp of the semi-rigid shell 70 comprise an opening 71 which extends vertically along the leg opposite the antero-external accommodation of the tibial cone intended to be placed therein and which extends over the vamp opposite the outer edge of the foot above the cuboid; the front end of this opening 71 is disposed transversely above the last two metatarsal ranges. Shell 70 has, in the zone of the internal malleolus, an attachment point 72 intended to fix the lower end 6b of the tibial lever 6 of the apparatus according to the invention. The opening 71 allows an easy accommodation of the foot and lower tibial cone within shell 70. Moreover, this opening gives a degree of freedom which ensures the dynamic equilibrium of the movement of the handicapped foot. Within the shell 70, on sole 701, is a support sole (not visible in the drawing) moulded to the shape of the plantar arch of the subject in the vertical equilibrium position.

The boot according to the invention comprises a reinforcing structure inserted on the shell and comprising a spring strip 73 and elastic adjusting means 74, 75 and 77.

The spring strip 73 is connected to the shell 70 at least by its two ends. In the embodiment described, the spring strip 73 is bonded externally to the shell 70 only at its two ends; it is constituted by a tempered steel strip 40 mm wide and 1 mm thick. In a variant, this spring strip might be embedded in the shell 70 as an insert during moulding of this shell. The spring strip 73 is disposed vertically opposite the fibula from the outer side of the heel bone as far as the zone of the top edge 702 of the shell; it is visible in FIG. 6.

The elastic adjusting means are formed by a multiplicity of elastic webs which compensate and regulate the action of the spring strip 73 and the tibial lever 6.

One elastic web 74 is stretched from a point at the level of the sole 701 on the postero-internal side of the heel, as far as the top edge 702 of the leg of shell 70. The web 74 makes an angle of approximately 30° with the vertical; it constitutes an elastic restraint regulating the movements of the inner side of the boot and promoting the internal screwing motions.

An elastic web 75 is disposed from the same point of the inner edge 701a of sole 701; it extends as fars as the implantation point 72 of the tibial lever 6 and constitutes an elastic restraint regulating the action of the lever 6 on boot 7.

An elastic web 77 is stretched between the attachment point 72 of the lever 6 and a point situated in the postero-external zone 701c of the outer edge 701b of sole 701; this elastic web 77 also acts as a means of closure of the boot since it passes above opening 71 at the level of the foot movement.

Boot 7 moreover comprises closing means, some of which also have the function of an elastic restraint in the course of movement. For this purpose, an elastic web 76 is stretched between a point situated on the inner edge 701a of sole 701 opposite the first metatarsal and a point situated on the external edge 701b of sole 701 at the level of the external edge of the cuboid. This elastic web 76 regulates the movements of the top part 703 of the boot vamp and ensures, at the same time, closure of the boot because it is disposed transversely in relation to opening 71. One could possibly position another optional elastic web 76a which proceeds from the same point of the internal edge 701a as the elastic web 76 and which proceeds to a point of the external edge 701b of sole 701 situated opposite the fifth metatarsal. The top part of the leg of shell 70 is closed by a closing web 78 disposed all along border 702. Finally, a web 79 disposed all around sole 701 grips all the insertion points of the elastic means disposed at the level of sole 701. All the elastic webs appearing in the make up of boot 7 advantageously have an adjustable length so as to be adjusted to the characteristics of the subject using the apparatus.

It will be found that the use of such a boot allows a slight physiological flexion of the ankle in the course of the subject's displacement, as well as the progress of the podal step (heel–external edge–internal edge).

Although the invention has been described with reference to a particular embodiment, it shall be duly understood that it is in no way restricted thereto and that various modifications of form and material may be brought thereto without thereby departing either from its scope or its spirit. In particular, the elastic straps of the apparatus, or the elastic web of the boots of the said apparatus, may be constituted not only from elastic materials or rubber bands but they may also be constituted of any element capable of exerting an elastic tension between the two points of attachment of these straps or bands. One could envisage making them of non-elastically deformable parts interconnected by an element capable of ensuring a regulation of the tension between these parts, for instance, by an appropriate electronic or mechanical means.

I claim:

1. External apparatus for the vertical stance and walking for a person with handicap of the motor system of one or two lower limbs, comprising, in combination:
   (a) a single piece corset disposed at the height of the pelvic girdle of the wearer;
   (b) parallel to the side of the femur of the wearer and over its length, an outer femoral lever comprising a strip of flexible metal capable of absorbing and restoring the flexural and torsional stresses;
   (c) at knee level of the wearer, a knee piece capable of maintaining the relative movements between the thigh and the leg in slight flexion and slight valgus position, within the strict limits of the physiological articular play;
   (d) parallel to the antero-internal side of the tibia of the wearer and over its whole length, an antero-inner lever comprising a strip of flexible metal capable of absorbing and restoring the flexural and torsional stresses;
   (e) a first elastic strap connecting the upper end of the outer femoral lever, substantially as an extension of the outer femoral lever, to the said corset in the vicinity of the iliac crest of the wearer;
   (f) a second elastic strap extending transversely whilst sloping slightly upwardly connecting the outer femoral lever to the corset towards or in the direction of the iliac spines of the wearer, the second elastic strap thus substantially crossing the pubic symphysis of the wearer;
   (g) means connecting the lower end of the femoral lever to the knee piece;
   (h) means connecting the upper end of the tibial lever to the knee piece; and
   (i) means limiting the articular play of the tibio-tarsal articulation of the wearer, and connected to the lower end of the tibial lever.

2. Apparatus according to claim 1, including means for adjusting the length of said first and second elastic straps.

3. Apparatus according to claim 1, wherein said femoral lever has a substantially sub-trochanteric upper end and a lower end which is substantially above the condyle of the wearer.

4. Apparatus according to claim 1, wherein the tibial lever has a top end which is substantially below the articulation and a lower end which is substantially above the malleolus of the wearer.

5. Apparatus according to any one of claims 1 to 4, wherein the knee piece comprises a plurality of straps constituting restraints to recurvation to the varus and valgus states, to flexion, as well as to internal and external rotations.

6. Apparatus according to claim 5, including means for adjusting the length of said knee piece straps.

7. Apparatus according to one of claims 1 to 4, wherein said means for limiting the articular play of the tibio-tarsal articulation of the wearer is an orthopaedic boot.

8. Apparatus according to claim 7, wherein the orthopaedic boot comprises:
   (i) a semi-rigid shell, defining a sole and a vamp, and surrounding the foot and the lower tibial cone of the wearer;
   (ii) means defining an opening in said shell, said opening extending opposite the antero-external accommodation of the tibial cone and opposite the outer edge of the foot of the wearer, above the cuboid and at least one metatarsal range;

(iii) securing means on said shell, in the zone of the internal malleolus of the wearer, for the lower end of the tibial lever;

(iv) elastic supporting means comprising, on the one hand, a spring strip fastened to the shell and disposed vertically opposite the fibula of the wearer, from the external side of the calcaneus as far as the zone of the upper edge of the shell and, on the other hand, elastic adjusting means outside the shell, extending firstly from the inner edge of the sole of the shell towards the upper part of the vamp and towards the upper edge of the leg of the shell and secondly, from said fixing means for the tibial lever to the postero-external zone of the heel of the sole; and (v) means for closing the shell of the boot.

9. Apparatus according to claim 8, wherein said means for closing the shell comprise elastic means stretched between the inner edge of the sole of the shell, at the level of the first metatarsal of the wearer, and the outer edge of the said sole, at the level of the cuboid of the wearer.

10. Apparatus according to claim 8, wherein the means for closing the shell comprise an elastic means stretched between the inner edge of the sole of the shell at the level of the first metatarsal of the wearer and the outer edge of the said sole, at the level of the fifth metatarsal of the wearer.

11. Apparatus according to claim 8, wherein, at the foot end, the opening of the shell extends transversely above the last two metatarsals.

12. Apparatus according to claim 8, wherein the shell surrounds the lower tibial cone over a distance covering at least the lower third of the leg of the wearer, and the closing means comprise a tightening band extending all along the upper edge of the leg of the shell.

13. Apparatus according to claim 8, wherein the shell of the boot is integrally moulded of a plastic material.

14. Apparatus according to claim 7, wherein the boot comprises internally a support sole for the foot, moulded to the shape of the plantar arch of the wearer when the wearer is in the vertical equilibrium position.

* * * * *